(12) United States Patent
Bonetto et al.

(10) Patent No.: US 12,402,801 B2
(45) Date of Patent: Sep. 2, 2025

(54) PATHOLOGIES DIAGNOSIS USING A SPECTRAL ELECTRICAL IMPEDANCE DEVICE

(71) Applicant: IMPEL IP, LLC, Wilmington, DE (US)

(72) Inventors: Fabián José Bonetto, Rio Negro (AR); Mario Joaquín Saravia, Ciudad Autónoma de Buenos Aires (AR); Mariela Inés Bellotti, Rio Negro (AR)

(73) Assignee: IMPEL IP, LLC, Wilmington, DE (US)

( * ) Notice: Subject to any disclaimer, the term of this patent is extended or adjusted under 35 U.S.C. 154(b) by 0 days.

(21) Appl. No.: 18/857,631

(22) PCT Filed: Apr. 21, 2023

(86) PCT No.: PCT/US2023/019327
§ 371 (c)(1),
(2) Date: Oct. 17, 2024

(87) PCT Pub. No.: WO2023/205373
PCT Pub. Date: Oct. 26, 2023

(65) Prior Publication Data
US 2025/0120607 A1    Apr. 17, 2025

Related U.S. Application Data

(60) Provisional application No. 63/333,799, filed on Apr. 22, 2022.

(51) Int. Cl.
*A61B 5/00*    (2006.01)
*A61B 3/10*    (2006.01)
*A61B 5/0538*    (2021.01)

(52) U.S. Cl.
CPC ............ *A61B 5/0538* (2013.01); *A61B 3/101* (2013.01); *A61B 5/6821* (2013.01); *A61B 5/725* (2013.01);

(Continued)

(58) Field of Classification Search
CPC ...... A61B 5/0538; A61B 3/101; A61B 5/6821; A61B 5/725; A61B 5/7253; A61B 2560/0468
See application file for complete search history.

(56) References Cited

U.S. PATENT DOCUMENTS

| 8,922,366 B1 * | 12/2014 | Honore | G02C 11/10 |
| | | | 351/158 |
| 2001/0028309 A1 * | 10/2001 | Torch | A61B 5/1103 |
| | | | 340/576 |

(Continued)

OTHER PUBLICATIONS

International Search Report & Written Opinion issued in corresponding International Application No. PCT/US2023/019327 dated Jul. 17, 2023, pp. 1-8.

(Continued)

*Primary Examiner* — May A Abouelela
(74) *Attorney, Agent, or Firm* — Carter, DeLuca & Farrell LLP

(57) ABSTRACT

A medical device and method of using the medical device include de following: (a) a device capable of generating a sinusoidal voltage at a fixed initial frequency for a specified time followed by a logarithmic sweep between that initial frequency and a final frequency in a total time of 0.5 seconds; and (b) one or several live microelectrodes and one ground electrode, all of them electrically separated by electrically insulating regions; (c) a strategy to obtain the experimental electrical resistance and capacitance values as a function of the excitation frequency of the sweep mentioned in a); and (d) an artificial intelligence, machine learning, linear discriminant analysis method to determine whether the patient has an ocular pathology or not based on the measurement of the electrical resistance and capacitance as a function of frequency in 0.5 seconds.

5 Claims, 4 Drawing Sheets

(52) U.S. Cl.
CPC .... *A61B 5/7253* (2013.01); *A61B 2560/0468* (2013.01)

(56) References Cited

U.S. PATENT DOCUMENTS

| | | | |
|---|---|---|---|
| 2002/0085174 A1* | 7/2002 | Bolger | A61B 3/113 351/209 |
| 2004/0127778 A1* | 7/2004 | Lambert | G01N 21/65 600/318 |
| 2004/0212781 A1* | 10/2004 | Mihashi | A61B 3/101 351/221 |
| 2006/0100488 A1* | 5/2006 | Davies | A61B 5/4381 600/306 |
| 2011/0212090 A1* | 9/2011 | Pedersen | A61K 40/4273 424/234.1 |
| 2012/0245444 A1* | 9/2012 | Otis | G02C 7/04 600/345 |
| 2015/0029463 A1* | 1/2015 | Hetling | A61B 5/398 351/219 |
| 2015/0065905 A1* | 3/2015 | Pugh | A61B 5/24 600/544 |
| 2015/0342723 A1* | 12/2015 | Abramson | A61B 5/11 623/6.64 |
| 2016/0147301 A1* | 5/2016 | Iwasaki | G06F 3/013 345/157 |
| 2016/0213242 A1 | 7/2016 | Trese | |
| 2016/0259180 A1* | 9/2016 | Liu | G02C 11/10 |
| 2016/0270656 A1* | 9/2016 | Samec | A61B 3/1035 |
| 2018/0032665 A1 | 2/2018 | Tang | |
| 2018/0173013 A1* | 6/2018 | Robillotto | A61B 5/7225 |
| 2019/0117109 A1* | 4/2019 | Grundfest | A61B 5/4875 |
| 2020/0093366 A1* | 3/2020 | Toner | G02C 7/04 |
| 2022/0330813 A1* | 10/2022 | Raymond | A61B 3/102 |
| 2023/0020468 A1* | 1/2023 | Kubota | G01B 9/02004 |
| 2023/0035094 A1* | 2/2023 | Belmonte Martínez | A61F 9/0008 |
| 2023/0190523 A1* | 6/2023 | Hahn | A61N 1/0448 604/294 |
| 2024/0164653 A1* | 5/2024 | Yu | A61B 5/7257 |

OTHER PUBLICATIONS

International Preliminary Report on Patentability issued in corresponding International Application No. PCT/US2023/019327 dated Oct. 11, 2024, pp. 1-19, with Article 34 Amendments.

* cited by examiner

PATHOLOGIES DIAGNOSIS USING A SPECTRAL ELECTRICAL IMPEDANCE DEVICE

CROSS REFERENCE TO RELATED APPLICATIONS

This application is a national stage application of International Application No. PCT/US23/19327, filed on Apr. 21, 2023, which claims the benefit of and priority to U.S. Provisional Application No. 63/333,799, filed Apr. 22, 2022, the disclosures of each of which are incorporated herein by reference in their entirety.

FIELD

The present invention relates to a device for sensing electrical signals of a patient's surface zone of the cornea and the conjunctiva, surface zone of the retina, surface zone of the skin (for skin cancer), bone bulk (for bone cancer), cell monolayer in culture (for a variety of cancers), and tumor surface (to determine whether benign or not). In the case of the cornea and conjunctiva, these living cells are sensed in vivo, in vitro and in situ in conjunction with the tear layer. The device uses electronic means in the minimum time and a strategy to determine the health of the sensed tissue/dispersed cells based on the signals.

BACKGROUND OF THE INVENTION

Tearlab has a technique that extracts a fraction of a tear of a patient and measures the osmolarity (through the electrical resistance of the small droplet) to determine the presence of Dry Eye Syndrome (DES).

One of the disadvantages of this method is that it has not been demonstrated (see Nice, for example) that the DES is directly related to the resistivity of the tear droplet which is the variable measured by the Tearlab device. Also, the Tearlab device can only discriminate the DES syndrome in the best of the cases.

The present device has a proven capacity to classify several different illnesses, conditions and syndromes such as DES, Sjogren, Pefingoid-Foster and Conjunctivitis among others, as well as pathologies based on the measurement of the electrical signals and the measurement of the spectral electrical resistance and capacitance in cornea, conjunctiva and retina, the zone immediately adjacent to the surface of the skin (for skin cancer), the bulk bone (for bone cancer), a cell monolayer in culture (for a variety of cancers included cancer of the tissue adhered to the external bone surface), the surface of a tumor (to detect whether benign or not in a direct manner).

SUMMARY OF THE INVENTION

The present invention detects:
1) ocular pathologies which were previously difficult to follow in any but a qualitative manner; the invention has been used to detect pathologies such as Dry Eye Syndrome which is, according to experts, a group of conditions and not a single condition, Pemphigoid-Foster, Sjogren and chronic conjunctivitis, in the surface of the eye;
2) attached and detached retina; it could also be used for histologically characterizing co-relationships of ocular tumors, among them choroidal melanoma, choroidal nevus, sectoral structure and function, degenerative diseases of the retina for intraoperative functional prognosis of the macula;
3) skin cancer (at the zone immediately adjacent to the surface of the skin);
4) bone cancer (at the bulk bone);
5) a variety of cancers included cancer of the tissue adhered to the external bone surface (at a cell monolayer in culture); and
6) whether a tumor is benign or not in a direct manner (at the surface of a tumor).

According to the invention, electrodes are made of Pt, Au or W. AC current of about 10 microamperes at varying frequencies is applied between a large counter electrode and a small active electrode and eventually a shielding electrode, while the voltage is monitored with a newly developed device described below.

Since this is a two probe measurement, the active electrode is made small, so that its impedance dominates the measurement. In the apparatus of the invention, measured cells can be from the eye cornea, conjunctiva or retina, from the zone immediately adjacent to the surface of the skin (for skin cancer), from the bulk bone (for bone cancer), from a cell monolayer in culture (for a variety of cancers included cancer of the tissue adhered to the external bone surface), and from the surface of a tumor (to detect whether benign or not in a direct manner). All dispersed tissues and cells are in direct contact with the electrodes.

In one application, the electrode impedance has been modeled by assuming that current flows uniformly and radially through the tear-film space, which is a fluid beneath the eyelids and above the surface of the eye (cornea or conjunctiva). Using impedance measurements over a range of alternating current (AC) frequencies, the average tear-film thickness can be calculated.

A new device is used to predict and minimize experimental errors in electrical impedance measurements in this type of apparatus using phase sensitive electronic devices working with time-varying excitation frequency. The reference frequency can be swept in order to measure the frequency response of a system within a given spectrum in a minimum possible time (0.5 seconds).

Figure 1A:
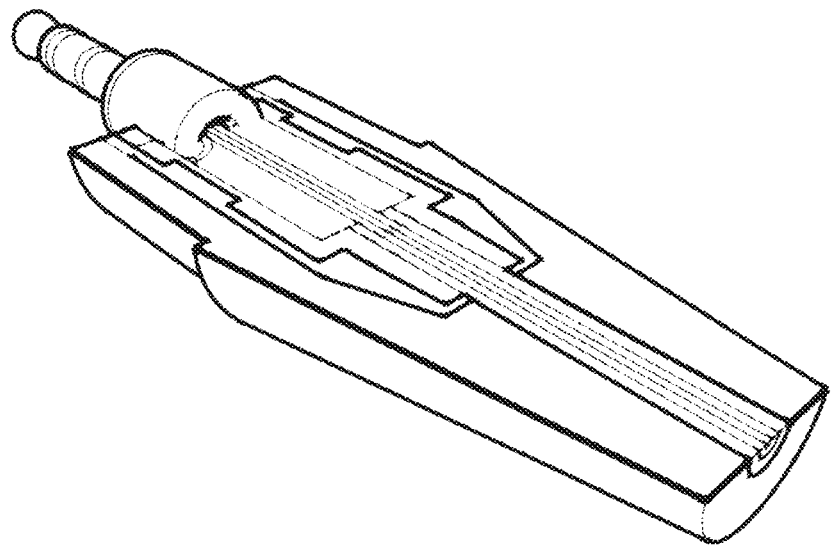
FIGS. 1A and 1B illustrate the corneal and conjunctival sensors respectively. The two bodies are made of acrylic and hold a hollow surgical steel cylinder (ground) and a 200-micron diameter gold wire separated by a biocompatible insulating adhesive. The two electrical connectors are connected to a stereo or bipolar connector to an external circuit.
Figure 1B:
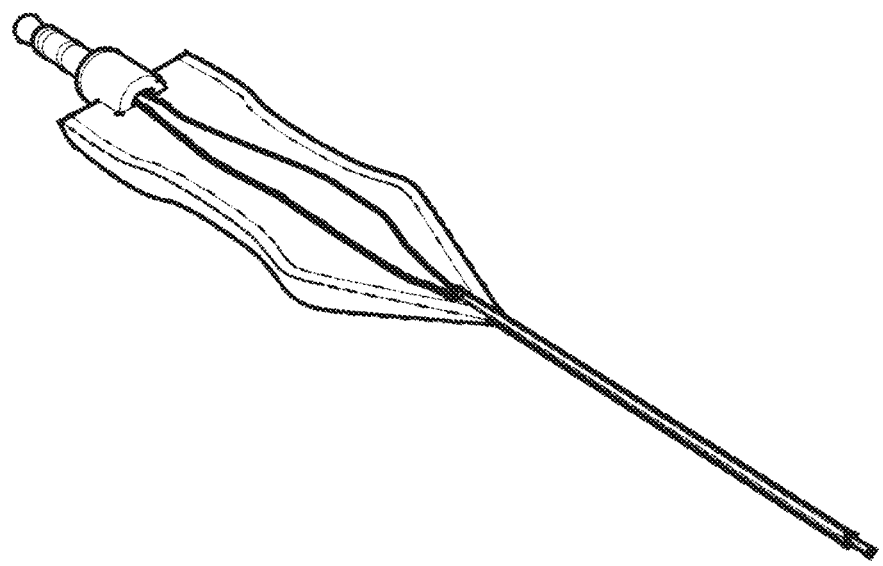

The sensors corresponding to other healthy or pathological tissue determinations are similar to those shown in FIGS. 1A and 1B. These determinations are related to a sensor of FIGS. 1A and 1B in contact with:
1) the zone immediately adjacent to the surface of the skin (for skin pathologies);
2) a cell monolayer obtained through disruption of a tissue cultivated in vitro (for a variety of pathologies including pathologies of the tissue adhered to the external and internal surfaces of bone); and
3) the surface of a tumor (to detect whether benign or not with a direct measurement).

Exceptionally, the measurement on bone is conducted in a standard plug, which is a cylinder 3 mm in diameter and 5 mm high. The spectral electric impedance is measured between the 2 opposite faces of the sample.

Figure 2:
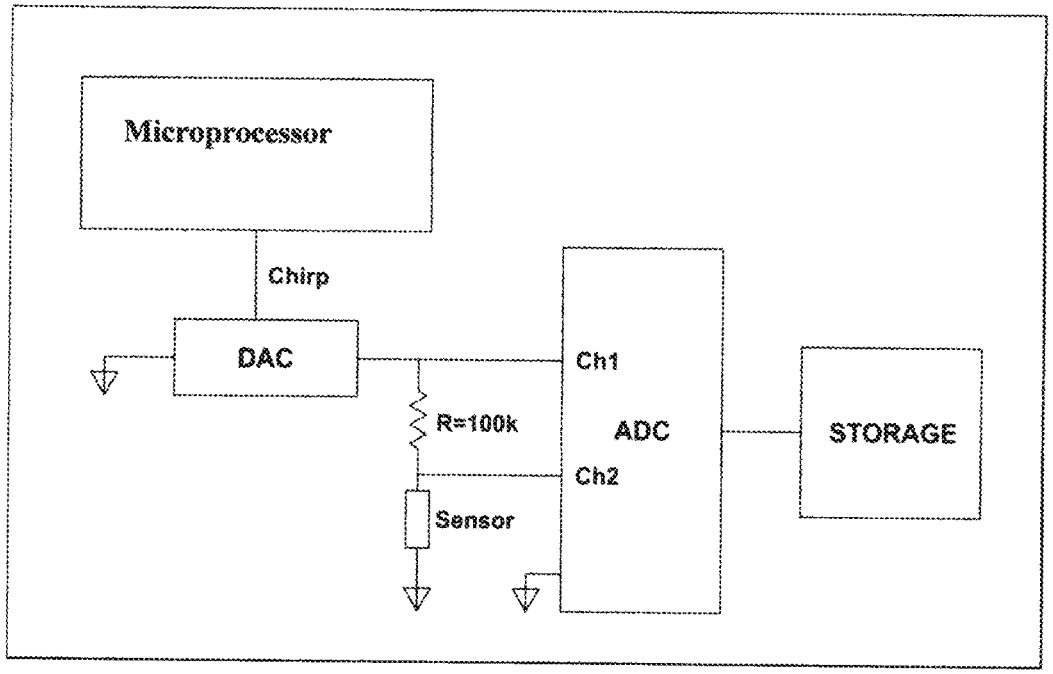

FIG. 2 shows a scheme of the detecting device/apparatus which functions as follows: A microprocessor produces a logarithmic chirp from the initial frequency to the final frequency intended to be measured digitally in the spectrum. The microprocessor feeds an analogic digital converter that stimulates the corresponding sensor through a load resistance (usually of about 100 kOhm). A two-channel analogic digital converter (channel 1 Ch1, and channel 2 Ch2) takes two signals and digitizes them. Channel 1 digitizes the DAC output and Ch2 takes the signal of the sensor. The DAC output stores the signal at the Storage unit.

Figure 3:
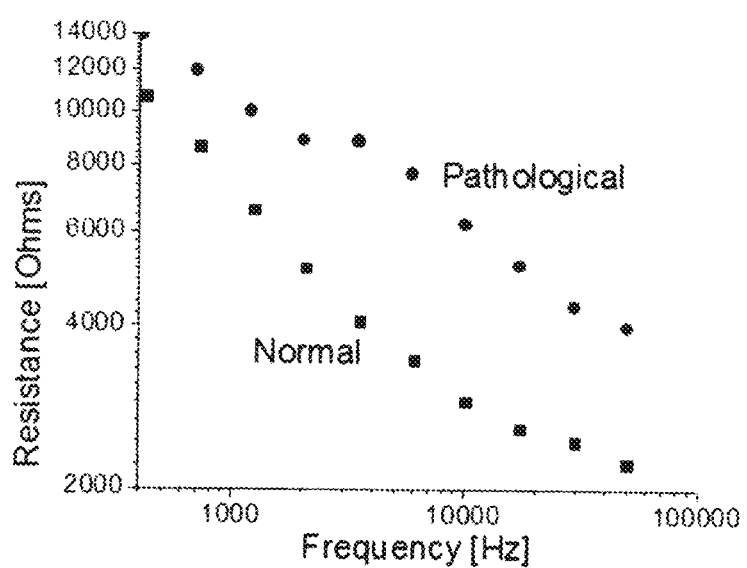

FIG. 3 illustrates the results for the application of a constant (0.1 Volt through a 1 MOhm resistor, 0.1 microAmp maximum) AC signal with a frequency span between 500 Hz to 64 kHz logarithmically spaced. This figure shows the electrical resistance as a function of applied frequency (spectral resistance) for a normal (healthy) cornea (filled squares) and for a pathological (Pemphigoid Foster-Dry Eye Syndrome) cornea (filled circles).

Figure 4:
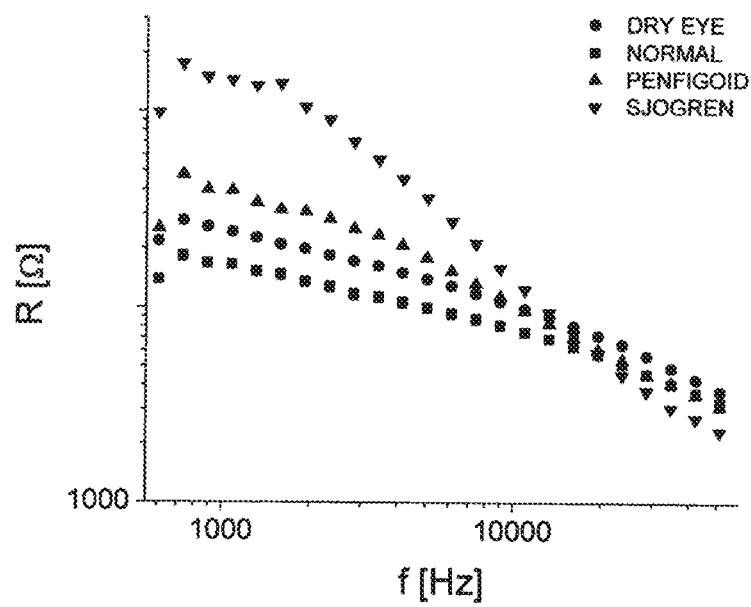

FIG. 4 is a resistance vs. frequency graph corresponding to the experiment conducted with patients suffering from Sjogren Syndrome, Pemphigoid and Dry Eye Disease, and healthy subjects (See Experimental section).

Figure 5:
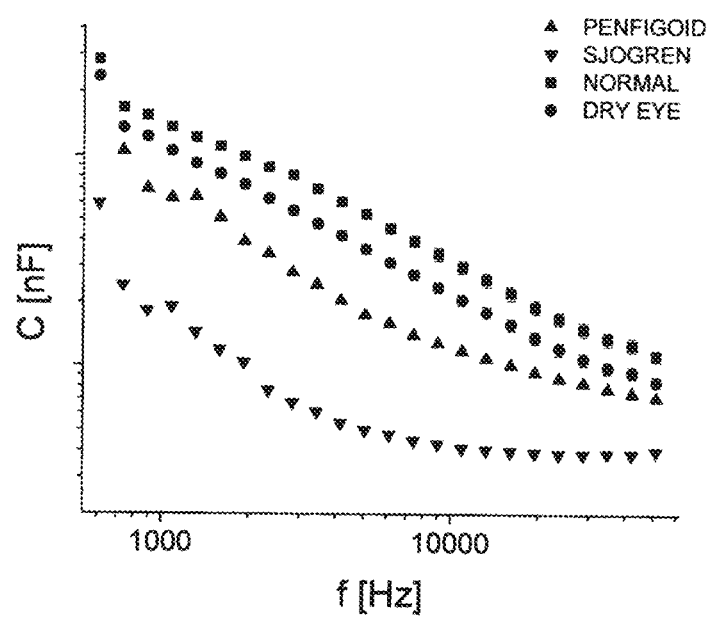

FIG. 5 is the capacitance vs. frequency graph corresponding to the experiment conducted with patients suffering from Sjogren Syndrome, Pemphigoid and Dry Eye Disease, and healthy subjects (See Experimental section).

Figure 6:
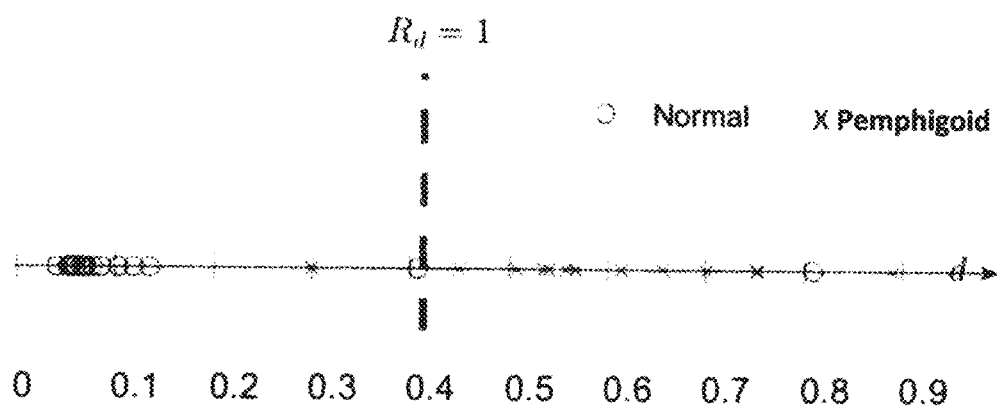

FIG. 6 shows as black circles and red crosses normal (healthy) and pathological (Pemphigoid Foster-Dry Eye Syndrome) eye surface populations. The dashed blue line located at d=0.405 represents the boundary between both populations as explained below, i.e. Rd=1. The model classifies a new data point as normal if it is at the left side of this boundary (Rd<1), and as pathological otherwise. It results for this case in about 5% of false positives and only one data point corresponding to Pathological eyes misclassified, yielding approximately 5% of false negatives. Similar results have been obtained with the sensor applied to different dispersed tissues and cells with the proposed sensor and with the bone measurement in the cylindrical sample.

DESCRIPTION OF THE PREFERRED EMBODIMENT

The present invention refers to a medical device and method of using same, comprising:
(a) a device capable of generating a sinusoidal voltage at a fixed initial frequency for a specified time followed by a logarithmic sweep between that initial frequency and a final frequency in a total time of 0.5 seconds;
(b) one or several live microelectrodes and one ground electrode, all of them electrically separated by electrically insulating regions;
(c) a strategy to obtain the experimental electrical resistance and capacitance values as a function of the excitation frequency of the sweep mentioned in a); and
(d) an artificial intelligence, machine learning, linear discriminant analysis method to determine whether the patient has an ocular pathology or not based on the measurement of the electrical resistance and capacitance as a function of frequency in 0.5 seconds.

The electrode consisting of the microelectrode, insulator and ground is adapted to contact soft tissue on the conjunctiva, the cornea, the ocular surface or the retina of the eye. The electrode is held by a manual spring loaded system to apply a constant pressure on the conjunctiva or the cornea. For the case of the retina, it is held by an ophthalmologist.

In further embodiments of the present invention, the electrode consisting of the microelectrode, insulator and ground is adapted to contact the zone immediately adjacent to the surface of the skin (for skin cancer), the bulk bone (for bone cancer), a cell monolayer in culture (for a variety of cancers included cancer of the tissue adhered to the external bone surface), and the surface of a tumor (to detect whether benign or not in a direct manner).

The device of the invention is capable of applying a frequency sweep of a frequency between 500 Hz and 64 kHz continuous in time with a logarithmic ramp. The device has to assure that the current circulating through the eye is less than 10 microAmp and the voltage drop is less than 1 Volt RMS between each microelectrode pair. Internally, the voltage device has a maximum voltage of 1 Volt RMS as reference voltage, and a load resistance of 0.1 MOhm that assures the conditions mentioned above.

The current applied between the small microelectrode and large counter microelectrode produces a voltage (signal voltage) which is monitored by a digitizer which samples the data at 1 MegaSample/sec during 0.5 seconds. The data is transferred to a dedicated electronic where it is processed and the spectral electrical impedance (electrical resistance and capacitance as a function of the frequency) is computed.

The reference voltage (applied signal) is scaled to a maximum amplitude of one and multiplied point by point by the signal voltage being the result low pass filtered with a Butterworth low pass filter. This is the real output component (resistance) of the Lock In amplifier. The way the imaginary component (capacitance) is obtained is explained below. The short overlapping window Fourier transform of the reference voltage is computed to obtain 25 logarithmically equally spaced frequency ranges averaging the filtered in phase and out of phase (quadrature) signals.

This result is the complex average Lock In signal. For each frequency range, the reference RMS minus the complex signal divided by the load resistance gives the complex current circulating through the circuit. The complex average signal voltage is divided by the complex current obtaining the electrical impedance. The real part gives the resistance and the minus imaginary part gives the reactance. The capacitance is obtained from the reactance.

Spectral resistance and capacitance data are supplied to and stored and processed within a personal computer, which shows the results on a display, which may be a video display.

Particularly, the electrode arrangement, and a processor related to the electrode, wherein the electrode is electrically connected to a source of alternating voltage with a frequency varying continuously within the range of frequencies of interest in a short period with variable amplitude, the electrode being subjected to that alternating current.

When the electrode comes in contact with the eye, for instance cornea, conjunctiva or retina, an electrical connection occurs between the electrodes to form an electrical circuit, and an electrical current flows between the microelectrodes through the corresponding ocular surface. This current produces a voltage with a frequency that is continuously varying with time and constitutes the primary signal used in this disclosure.

In further embodiments of the present invention, the electrode comes in contact with the zone immediately adjacent to the surface of the skin (for skin cancer), the bulk bone (for bone cancer), a cell monolayer in culture (for a variety of cancers included cancer of the tissue adhered to the external bone surface), and the surface of a tumor (to detect whether benign or not in a direct manner), and an electrical current flows between the microelectrodes through the corresponding surface. This current produces a voltage with a frequency that is continuously varying with time and constitutes the primary signal used in this disclosure.

The following describes how the experimental resistance and capacitance values are obtained at values as low as 0.5 seconds in continuous frequency ranges from 500 Hz to 50 kHz. The analog voltage is fed to a device that digitizes and processes the voltage signal of the electrode. From this processed signal the impedance of the ocular surface as a function of frequency is obtained.

What follows shows how to obtain the capacitance component in the proposed electronic device in 0.5 seconds.

A reference voltage signal VR(t) is applied to the microelectrode in series with a load resistor RL and is digitized at a sampling rate $f_S$, typically 1 MSa/s. The voltage drop across the microelectrode $V_E(t)$ is also digitized simultaneously. The reference signal $V_R$ is normalized to an amplitude of 1. This is multiplied instant by instant with $V_E$ and called p'(t,f).

Taking the Hilbert transform of the signal p'(t,f), the signal q'(t,f) is obtained which is in quadrature with p'(t,f) frequency by frequency, and is multiplied with $V_E$ obtaining q(t,f). The values of p'(t,f) and q'(t,f) are passed through a low-pass filter to obtain p(t,f) and q(t,f), respectively. With the complex values of voltage (obtained from p and q) and the complex values of electric current (obtained from $V_R$, $R_L$ in addition to p and q), the values of R and C are window averaged in 25 discrete values.

EXPERIMENTAL

Methods: A cohort of 62 patients was divided into 4 groups according to confirmed diagnosis: Sjogren Syndrome (antiRO and AntiLa positive test), Pemphigoid (biopsy and histology positive), Dry Eye Disease (OSDI and BUT positive) and healthy controls (also diagnosed by OSDI and BUT).

Each cornea was measured twice in different loci with up to 2 min interval to evaluate reproducibility. By direct apposition of a sensor (200 micron diameter gold disk microelectrode) with the corneal surface for at least one second we got a unique register of resistance and capacitance to the electric current delivered. Patients were evaluated for any corneal distress.

Results: Data from 244 measures obtained from 122 corneas were analyzed.

Safety Evaluation of corneas after the procedure was uneventful, showing it is safe to obtain ESI registers in patients with corneal diseases by this means. All the measures resulted effective, so there was no need to repeat any.

Reproducibility ESI determinations in each cornea resulted quite similar within a narrow range of dispersion, which demonstrated reproducibility of the tool.

Objectivity Data from different subjects of the same group were consistent. FIGS. 4 and 5 show the consistency of the curve of different severe conditions as Pemphigoid and Sjogren in significant difference from the control curve.

Conclusions: Measuring ESI in corneas with our experimental device is a safe procedure and could be a new tool to differentiate corneal conditions from healthy corneas with an objective determination, which would be of help in improving the diagnosis of Dry Eye Disease and other corneal pathologies.

A particular algorithm of Artificial Intelligence (AI), of the class of Machine Learning (ML) type, called Linear Discriminant Analysis (LDA), described more precisely below, is used to associate a set of measured impedance values as a function of frequency to determine if a patient's eye has a pathology or not. The results are illustrated with corneal data, but similar results were unexpectedly obtained with conjunctiva and retina.

The objective of the LDA algorithm is to find a unit vector w (in the space of the features) that maximizes the ratio of inter- and intra-population dispersion when the experimental points are projected on it, allowing a maximum separation between populations. The intra-population dispersion SW is given between the points of each population separately, and gives an idea of how dispersed the values of each one are (low values indicate that the point cloud is highly concentrated). On the other hand, the inter-population dispersion SB is associated with the distance between the population means, and it is greater the further apart their means are from each other. The LDA method maximizes the SB/SW ratio, and therefore allows a maximum separation between both populations.

Before using the discrimination algorithm, a dimensional reduction is carried out based on feature selection results of practical importance, which provides a better insight on the problem by focusing only on those features that give a significant separation between both populations. We consider as features the measured frequencies f and the corresponding Z impedances. We considered values of $p<1\times10^{-3}$ as most significant and selected only those features that presented this condition simultaneously under the Kolmogorov-Smirnov test and one of other two tests (the F test and the Student's t test). Following this criterion, 12 of the initial 17 features (frequencies) are relevant in terms of their discriminant capacity. Hence, the analysis that follows is based on this 12-dimensional feature vector.

The features of the model are the resistances and electrical capacitances for each frequency (dimension 25). As a demonstrative example, the case of normal patients (class 1) and those having the Pemphigoid Foster pathology (Dry Eye Syndrome, class 2) was taken. The scatter within each of the classes and the scatter between classes were calculated. The projection that maximizes the distance between classes by minimizing the scatter within classes was found. The distance to the origin of each point of each class on the estimated eigenvector was calculated, together with that of the values of each feature for each class by obtaining the value on the discrimination line. For each point of each class, the distance on the eigenvector to the respective class average was calculated to see if the quotient between distances to one or the other of the class averages is less or greater than 1. Based on these results, if they are greater or less than the average of the averages of the values of the two classes, discrimination is made if the eye is normal or has a pathology.

Data points are represented in FIG. 6 as black circles and red crosses for normal and pathological eye surface populations (Pemphigoid Foster-Dry Eye Syndrome), respectively for the final result. The dashed blue line located at d=0.405 represents the boundary between both populations, i.e., a hyperplane where the Euclidean distances to both population means are the same and, therefore, Rd=1. The model classifies a new data point as normal if its projection along w lays at the left side of this boundary (Rd<1), and as pathological if it lays at the right side of the boundary (Rd>1), given by:

$$dN = wT \cdot x - \mu N,$$
$$dL = wT \cdot x - \mu L,$$

where dN and μN are the Euclidean distance and population mean (projected onto w) corresponding to normal eyes, and dL and µL correspond to ill eyes. If these distances are considered as new features, the problem is reduced to one dimension.

The criterion to choose whether an unknown feature vector x comes from a normal or pathological eye is to measure the ratio between Euclidean distances Rd=dL/dN and to assume that values of Rd larger than 1 correspond to pathological eyes and values smaller than 1 represent normal eyes.

The size of the initial samples was 18 for normal eyes and 24 for pathological eyes. FIG. 6 shows the projections of the 12-dimensional feature vectors on the direction given by the discriminant unit vector w. The vertical line represents the hyperplane perpendicular to w for which Rd=1 and the experimental data points corresponding to both cell lines are scattered around it. As it can be observed, a clear separation between populations is achieved and only one data point corresponding to normal eyes is misclassified, yielding approximately 5% of false positives and only one data point corresponding to pathological eyes is misclassified, yielding approximately 5% of false negatives.

While a specific embodiment of the invention has been shown and described in detail to illustrate the application of the principles of the invention, it will be understood that the invention may be embodied otherwise without departing from such principles.

What is claimed is:

1. A device to measure a raw electrical digitized signal used in an algorithm using reference and sensor voltage measurements in order to calculate, as main parameters, resistance and capacitance as a function of frequency for measuring the raw electrical digitized signal of a patient's ocular surface and intraocular structures, at a minimum measurement time, comprising:
   a sensor including an electrode connected to the device consisting of at least a microelectrode, a material acting as an insulator, and a material acting as a ground, that is adapted to contact the patient's ocular surface and intraocular structures,
   wherein the device measures an impedance over a range of alternating current (AC) frequencies of the electrode when a current flows uniformly and radially through a tear film space above the patient's ocular surface, and
   wherein the device comprises a continuously variable frequency current source of logarithmic sweep, a voltage digitizer, a digital low pass filter system and sensitive phase detection algorithm using a Hilbert transform to obtain a quadrature signal from a reference signal.

2. The device according to claim 1, wherein the reference and sensor voltage measurements are used to calculate the resistance and capacitance as the function of frequency of the patient's ocular surface or intraocular structures selected from cornea, conjunctiva and surface zone of a retina, at the minimum measurement time.

3. The application of the device according to claim 1, wherein the reference and sensor voltage measurements are used to calculate the resistance and capacitance as the function of frequency of the patient's ocular surface of a cornea or a conjunctiva, at the minimum measurement time.

4. The device according to claim 1, wherein the reference and sensor voltage measurements are used to calculate the resistance and capacitance as the function of frequency over the range of AC frequencies, an average thickness of the tear film is calculated.

5. The device according to claim 1, wherein the reference and sensor voltage measurements are used to estimate the resistance and capacitance as the function of frequency of the patient's intraocular structures selected from iris, crystalline lens, optic nerve and retina, at the minimum measurement time.

* * * * *